US006313269B1

(12) United States Patent
Deen et al.

(10) Patent No.: US 6,313,269 B1
(45) Date of Patent: Nov. 6, 2001

(54) TUMOR NECROSIS FACTOR RELATED RECEPTOR, TR6

(75) Inventors: Keith C. Deen, Glenmore, PA (US); Peter R. Young, Lawrenceville, NJ (US); Lisa A. Marshall, Wyndmoor, PA (US); Amy K. Roshak, East Norriton, PA (US); Kong B. Tan, Philadelphia, PA (US); Alemseged Truneh, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/333,593

(22) Filed: Jun. 15, 1999

Related U.S. Application Data

(63) Continuation-in-part of application No. 08/916,625, filed on Aug. 22, 1997, which is a continuation-in-part of application No. 08/853,684, filed on May 9, 1997, now abandoned.

(60) Provisional application No. 60/041,230, filed on Mar. 14, 1997.

(51) Int. Cl.[7] ........................ C07K 14/715; C12N 15/12

(52) U.S. Cl. .......................................... 530/350; 435/69.1

(58) Field of Search .................................. 530/350, 351, 530/402; 435/69.1; 514/2, 8, 12

(56) References Cited

U.S. PATENT DOCUMENTS 6,072,047 * 6/2000 Ranch et al. ........................ 536/23.5

FOREIGN PATENT DOCUMENTS 0 911 633A1 4/1999 (EP) .
WO 98/46643 10/1998 (WO) .
WO 98/58062 A1 12/1998 (WO) .
WO 99/00423 A1 1/1999 (WO) .
WO 99/09165 A1 2/1999 (WO) .
WO 99/11791 A2 3/1999 (WO) .

OTHER PUBLICATIONS

Doerks, et al., "Protein annotation: detective work for function prediction". TIG. Jun. 1998, vol. 14, No. 6.

Bork, et al., "Go hunting in sequence databases but watch out for the traps". TIG. Oct. 1996, vol. 12, No. 10.

Macfarlane et al., "Identification and Molecular Cloning of Two Novel Receptors for the Cytotoxic Ligand TRAIL", Journal of Biology Chemistry, vol. 272, pp. 25417–25420 (1997).

Screaton et al., "TRICK2, a new alternatively spliced receptor that transduces the cytotoxic signal From Trail", Current Biology, vol. 7, pp. 693–696 (1997).

Walczak et al., "TRAIL–R2–a novel apoptosis–mediating receptor for TRAIL", EMBO Journal, vol. 16(17), pp. 5386–5397 (1997).

Sheridan et al., "Control of TRAIL–Induced Apoptosis by a Family of Signaling and Decoy Receptors", Science, vol. 277, pp. 818–821 (1997).

Pan et al., "An Antagonist Decoy Receptor and a Death Domain–Containin Receptor for TRAIL", Science, vol. 277, pp. 815–817 (1997).

* cited by examiner

*Primary Examiner*—Prema Mertz
(74) *Attorney, Agent, or Firm*—William T. Han; Ratner & Prestia; William T. King

(57) ABSTRACT

TR6 polypeptides and polynucleotides and methods for producing such polypeptides by recombinant techniques are disclosed. Also disclosed are methods for utilizing TR6 polypeptides and polynucleotides in the design of protocols for the treatment of chronic and acute inflammation, arthritis, septicemia, autoimmune diseases (e.g. inflammatory bowel disease, psoriasis), transplant rejection, graft vs. host disease, infection, stroke, ischemia, acute respiratory disease syndrome, restenosis, brain injury, AIDS, Bone diseases, cancer, atheroschlerosis, and Alzheimers disease, among others and diagnostic assays for such conditions.

2 Claims, No Drawings

SEQUENCE LISTING

```
<160> NUMBER OF SEQ ID NOS:  8

<210> SEQ ID NO 1
<211> LENGTH: 3881
<212> TYPE: DNA
<213> ORGANISM: HOMO SAPIENS
<220> FEATURE:
<221> NAME/KEY: UNSURE
<222> LOCATION: (3538)(3598)(3601)(3607)(3608)(3619)(3632)(3659)(3686)
      (3690)

<400> SEQUENCE: 1

ctttgcgccc acaaaataca ccgacgatgc ccgatctact ttaagggctg aaacccacgg     60

gcctgagaga ctataagagc gttccctacc gccatggaac aacggggaca gaacgccccg    120

gccgcttcgg gggcccggaa aaggcacggc ccaggaccca gggaggcgcg gggagccagg    180

cctgggcccc gggtccccaa gacccttgtg ctcgttgtcg ccgcggtcct gctgttggtc    240

tcagctgagt ctgctctgat cacccaacaa gacctagctc cccagcagag agcggcccca    300

caacaaaaga ggtccagccc ctcagaggga ttgtgtccac ctggacacca tatctcagaa    360

gacggtagag attgcatctc ctgcaaatat ggacaggact atagcactca atggaatgac    420
```

-continued

```
ctccttttct gcttgcgctg caccaggtgt gattcaggtg aagtggagct aagtccctgc    480
accacgacca gaaacacagt gtgtcagtgc gaagaaggca ccttccggga agaagattct    540
cctgagatgt gccggaagtg ccgcacaggg tgtcccagag ggatggtcaa ggtcggtgat    600
tgtacaccct ggagtgacat cgaatgtgtc cacaaagaat caggcatcat cataggagtc    660
acagttgcag ccgtagtctt gattgtggct gtgtttgttt gcaagtcttt actgtggaag    720
aaagtccttc cttacctgaa aggcatctgc tcaggtggtg gtggggaccc tgagcgtgtg    780
gacagaagct cacaacgacc tggggctgag gacaatgtcc tcaatgagat cgtgagtatc    840
ttgcagccca cccaggtccc tgagcaggaa atggaagtcc aggagccagc agagccaaca    900
ggtgtcaaca tgttgtcccc cggggagtca gagcatctgc tggaaccggc agaagctgaa    960
aggtctcaga ggaggaggct gctggttcca gcaaatgaag gtgatcccac tgagactctg   1020
agacagtgct tcgatgactt tgcagacttg gtgccctttg actcctggga gccgctcatg   1080
aggaagttgg gcctcatgga caatgagata aaggtggcta aagctgaggc agcgggccac   1140
agggacacct tgtacacgat gctgataaag tgggtcaaca aaaccgggcg agatgcctct   1200
gtccacaccc tgctggatgc cttggagacg ctgggagaga gacttgccaa gcagaagatt   1260
gaggaccact tgttgagctc tggaaagttc atgtatctag aaggtaatgc agactctgcc   1320
atgtcctaag tgtgattctc ttcaggaagt cagaccttcc ctggtttacc tttttttctgg   1380
aaaaagccca actggactcc agtcagtagg aaagtgccac aattgtcaca tgaccggtac   1440
tggaagaaac tctcccatcc aacatcaccc agtggatgga acatcctgta acttttcact   1500
gcacttggca ttatttttat aagctgaatg tgataataag gacactatgg aaatgtctgg   1560
atcattccgt ttgtgcgtac tttgagattt ggtttgggat gtcattgttt tcacagcact   1620
tttttatcct aatgtaaatg ctttatttat ttatttgggc tacattgtaa gatccatcta   1680
cacagtcgtt gtccgacttc acttgatact atatgatatg aacctttttt gggtgggggg   1740
tgcggggcag ttcactctgt ctcccaggct ggagtgcaat ggtgcaatct tggctcacta   1800
tagccttgac ctctcaggct caagcgattc tcccacctca gccatccaaa tagctgggac   1860
cacaggtgtg caccaccacg cccggctaat tttttgtatt ttgtctagat ataggggctc   1920
tctatgttgc tcagggtggt ctcgaattcc tggactcaag cagtctgccc acctcagact   1980
cccaaagcgg tggaattaga ggcgtgagcc cccatgcttg gccttacctt tctactttta   2040
taattctgta tgttattatt ttatgaacat gaagaaactt tagtaaatgt acttgtttac   2100
atagttatgt gaatagatta gataaacata aaaggaggag acatacaatg ggggaagaag   2160
aagaagtccc ctgtaagatg tcactgtctg ggttccagcc ctccctcaga tgtactttgg   2220
cttcaatgat tggcaacttc tacaggggcc agtcttttga actggacaac cttacaagta   2280
tatgagtatt atttataggt agttgtttac atatgagtcg ggaccaaaga gaactggatc   2340
cacgtgaagt cctgtgtgtg gctggtccct acctgggcag tctcatttgc acccatagcc   2400
cccatctatg gacaggctgg gacagaggca gatgggttag atcacacata acaatagggt   2460
ctatgtcata tcccaagtga acttgagccc tgtttgggct caggagatag aagacaaaat   2520
ctgtctcccc acgtctgcca tggcatcaag ggggaagagt agatggtgct tgagaatggt   2580
gtgaaatggt tgccatctca ggagtagatg gcccggctca cttctggtta tctgtcaccc   2640
tgagcccatg agctgccttt tagggtacag attgcctact tgaggacctt ggccgctctg   2700
taagcatctg actcatctca gaaatgtcaa ttcttaaaca ctgtggcaac aggacctaga   2760
```

-continued

```
atggctgacg cattaaggtt ttcttcttgt gtcctgttct attattgttt taagacctca   2820

gtaaccattt cagcctcttt ccagcaaacc cttctccata gtatttcagt catggaagga   2880

tcatttatgc aggtagtcat tccaggagtt tttggtcttt tctgtctcaa ggcattgtgt   2940

gttttgttcc gggactggtt tgggtgggac aaagttagaa ttgcctgaag atcacacatt   3000

cagactgttg tgtctgtgga gttttaggag tggggggtga cctttctggt ctttgcactt   3060

ccatcctctc ccacttccat ctggcatccc cacgcgttgt cccctgcact tctggaaggc   3120

acagggtgct gctgcttcct ggtctttgcc tttgctgggc cttctgtgca ggacgctcag   3180

cctcagggct cagaaggtgc cagtccggtc ccaggtccct tgtcccttcc acagaggcct   3240

tcctagaaga tgcatctaga gtgtcagcct tatcagtgtt taagattttt cttttatttt   3300

taattttttt gagacagaat ctcactctct cgcccaggct ggagtgcaac ggtacgatct   3360

tggctcagtg caacctccgc ctcctgggtt caagcgattc tcgtgcctca gcctccggag   3420

tagctgggat tgcaggcacc cgccaccacg cctggctaat ttttgtattt ttagtagaga   3480

cggggtttca ccatgttggt caggctggtc tcgaactcct gacctcaggt gatccacntt   3540

ggcctccgaa agtgctggga tatacaaggc gtgagccacc agccaggcca agatattntt   3600

ntaaagnnag cttccggang acatgaaata angggggtt ttgttgttta gtaacattng   3660

gctttgatat atccccaggc caaatngcan gngacacagg acagccatag tatagtgtgt   3720

cactcgtggt tggtgtcctt tcatggttct gccctgtcaa aggtccctat ttgaaatgtg   3780

ttataataca aacaaggaag cacattgtgt acaaaatact tatgtattta tgaatccatg   3840

accaaattaa atatgaaacc ttatataaaa aaaaaaaaaa a                        3881
```

<210> SEQ ID NO 2
<211> LENGTH: 412
<212> TYPE: PRT
<213> ORGANISM: HOMO SAPIENS

<400> SEQUENCE: 2

```
Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr Gln Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175
```

-continued

Glu Cys Val His Lys Glu Ser Gly Ile Ile Ile Gly Val Thr Val Ala
180 185 190

Ala Val Val Leu Ile Val Ala Val Phe Val Cys Lys Ser Leu Leu Trp
195 200 205

Lys Lys Val Leu Pro Tyr Leu Lys Gly Ile Cys Ser Gly Gly Gly Gly
210 215 220

Asp Pro Glu Arg Val Asp Arg Ser Ser Gln Arg Pro Gly Ala Glu Asp
225 230 235 240

Asn Val Leu Asn Glu Ile Val Ser Ile Leu Gln Pro Thr Gln Val Pro
245 250 255

Glu Gln Glu Met Glu Val Gln Glu Pro Ala Glu Pro Thr Gly Val Asn
260 265 270

Met Leu Ser Pro Gly Glu Ser Glu His Leu Leu Glu Pro Ala Glu Ala
275 280 285

Glu Arg Ser Gln Arg Arg Arg Leu Leu Val Pro Ala Asn Glu Gly Asp
290 295 300

Pro Thr Glu Thr Leu Arg Gln Cys Phe Asp Asp Phe Ala Asp Leu Val
305 310 315 320

Pro Phe Asp Ser Trp Glu Pro Leu Met Arg Lys Leu Gly Leu Met Asp
325 330 335

Asn Glu Ile Lys Val Ala Lys Ala Glu Ala Ala Gly His Arg Asp Thr
340 345 350

Leu Tyr Thr Met Leu Ile Lys Trp Val Asn Lys Thr Gly Arg Asp Ala
355 360 365

Ser Val His Thr Leu Leu Asp Ala Leu Glu Thr Leu Gly Glu Arg Leu
370 375 380

Ala Lys Gln Lys Ile Glu Asp His Leu Leu Ser Ser Gly Lys Phe Met
385 390 395 400

Tyr Leu Glu Gly Asn Ala Asp Ser Ala Met Ser Glu
405 410

<210> SEQ ID NO 3
<211> LENGTH: 1062
<212> TYPE: DNA
<213> ORGANISM: HOMO SAPIENS

<400> SEQUENCE: 3
atgacctcct tttctgcttg cgctgcacca ggtgtgattc aggtgaagtg gagctaagtc 60
cctgcaccac gaccagaaac acagtgtgtc agtgcgaaga aggcaccttc cgggaagaag 120
attctcctga gatgtgccgg aagtgccgca cagggtgtcc cagagggatg gtcaaggtcg 180
gtgattgtac accctggagt gacatcgaat gtgtccacaa agaatcaggc atcatcatag 240
gagtcacagt tgcagccgta gtcttgattg tggctgtgtt tgtttgcaag tctttactgt 300
ggaagaaagt ccttccttac ctgaaaggca tctgctcagg tggtggtggg gaccctgagc 360
gtgtggacag aagctcacaa cgacctgggg ctgaggacaa tgtcctcaat gagatcgtga 420
gtatcttgca gcccacccag gtccctgagc aggaaatgga agtccaggag ccagcagagc 480
caacaggtgt caacatgttg tcccccgggg agtcagagca tctgctggaa ccggcagaag 540
ctgaaaggtc tcagaggagg aggctgctgg ttccagcaaa tgaaggtgat cccactgaga 600
ctctgagaca gtgcttcgat gactttgcag acttggtgcc ctttgactcc tgggagccgc 660
tcatgaggaa gttgggcctc atggacaatg agataaaggt ggctaaagct gaggcagcgg 720
gccacaggga caccttgtac acgatgctga taaagtgggt caacaaaacc gggcgagatg 780

-continued

```
cctctgtcca caccctgctg gatgccttgg agacgctggg agagagactt gccaagcaga    840

agattgagga ccacttgttg agctctggaa agttcatgta tctagaaggt aatgcagact    900

ctgccatgtc ctaagtgtga ttctcttcag gaagtcagac cttccctggt ttaccttttt    960

tctggaaaaa gcccaactgg actccagtca gtaggaaagt gccacaattg tcacatgacc   1020

ggtactggaa gaaactctcc catccaacat cacccagtgg at                      1062


<210> SEQ ID NO 4
<211> LENGTH: 303
<212> TYPE: PRT
<213> ORGANISM: HOMO SAPIENS

<400> SEQUENCE: 4

Asp Leu Leu Phe Cys Leu Arg Cys Thr Arg Cys Asp Ser Gly Glu Val
 1               5                  10                  15

Glu Leu Ser Pro Cys Thr Thr Thr Arg Asn Thr Val Cys Gln Cys Glu
            20                  25                  30

Glu Gly Thr Phe Arg Glu Glu Asp Ser Pro Glu Met Cys Arg Lys Cys
        35                  40                  45

Arg Thr Gly Cys Pro Arg Gly Met Val Lys Val Gly Asp Cys Thr Pro
    50                  55                  60

Trp Ser Asp Ile Glu Cys Val His Lys Glu Ser Gly Ile Ile Ile Gly
65                  70                  75                  80

Val Thr Val Ala Ala Val Val Leu Ile Val Ala Val Phe Val Cys Lys
                85                  90                  95

Ser Leu Leu Trp Lys Lys Val Leu Pro Tyr Leu Lys Gly Ile Cys Ser
            100                 105                 110

Gly Gly Gly Gly Asp Pro Glu Arg Val Asp Arg Ser Ser Gln Arg Pro
        115                 120                 125

Gly Ala Glu Asp Asn Val Leu Asn Glu Ile Val Ser Ile Leu Gln Pro
    130                 135                 140

Thr Gln Val Pro Glu Gln Glu Met Glu Val Gln Glu Pro Ala Glu Pro
145                 150                 155                 160

Thr Gly Val Asn Met Leu Ser Pro Gly Glu Ser Glu His Leu Leu Glu
                165                 170                 175

Pro Ala Glu Ala Glu Arg Ser Gln Arg Arg Arg Leu Leu Val Pro Ala
            180                 185                 190

Asn Glu Gly Asp Pro Thr Glu Thr Leu Arg Gln Cys Phe Asp Asp Phe
        195                 200                 205

Ala Asp Leu Val Pro Phe Asp Ser Trp Glu Pro Leu Met Arg Lys Leu
    210                 215                 220

Gly Leu Met Asp Asn Glu Ile Lys Val Ala Lys Ala Glu Ala Ala Gly
225                 230                 235                 240

His Arg Asp Thr Leu Tyr Thr Met Leu Ile Lys Trp Val Asn Lys Thr
                245                 250                 255

Gly Arg Asp Ala Ser Val His Thr Leu Leu Asp Ala Leu Glu Thr Leu
            260                 265                 270

Gly Glu Arg Leu Ala Lys Gln Lys Ile Glu Asp His Leu Leu Ser Ser
        275                 280                 285

Gly Lys Phe Met Tyr Leu Glu Gly Asn Ala Asp Ser Ala Met Ser
    290                 295                 300


<210> SEQ ID NO 5
<211> LENGTH: 1769
<212> TYPE: DNA
```

-continued

<213> ORGANISM: HOMO SAPIENS

<400> SEQUENCE: 5

```
cctcactgac tataaaagaa tagagaagga agggcttcag tgaccggctg cctggctgac     60
ttacagcagt cagactctga caggatcatg gctatgatgg aggtccaggg gggacccagc    120
ctgggacaga cctgcgtgct gatcgtgatc ttcacagtgc tcctgcagtc tctctgtgtg    180
gctgtaactt acgtgtactt taccaacgag ctgaagcaga tgcaggacaa gtactccaaa    240
agtggcattg cttgtttctt aaaagaagat gacagttatt gggaccccaa tgacgaagag    300
agtatgaaca gcccctgctg gcaagtcaag tggcaactcc gtcagctcgt tagaaagatg    360
attttgagaa cctctgagga aaccatttct acagttcaag aaaagcaaca aaatatttct    420
cccctagtga gagaaagagg tcctcagaga gtagcagctc acataactgg gaccagagga    480
agaagcaaca cattgtcttc tccaaactcc aagaatgaaa aggctctggg ccgcaaaata    540
aactcctggg aatcatcaag gagtgggcat tcattcctga gcaacttgca cttgaggaat    600
ggtgaactgg tcatccatga aaaagggttt tactacatct attcccaaac atactttcga    660
tttcaggagg aaataaaaga aaacacaaag aacgacaaac aaatggtcca atatatttac    720
aaatacacaa gttatcctga ccctatattg ttgatgaaaa gtgctagaaa tagttgttgg    780
tctaaagatg cagaatatgg actctattcc atctatcaag gggggaatatt tgagcttaag    840
gaaaatgaca gaatttttgt ttctgtaaca aatgagcact tgatagacat ggaccatgaa    900
gccagttttt tcggggcctt tttagttggc taactgacct ggaaagaaaa agcaataacc    960
tcaaagtgac tattcagttt tcaggatgat acactatgaa gatgtttcaa aaaatctgac   1020
caaaacaaac aaacagaaaa cagaaaacaa aaaaacctct atgcaatctg agtagagcag   1080
ccacaaccaa aaaattctac aacacacact gttctgaaag tgactcactt atcccaagaa   1140
aatgaaattg ctgaaagatc tttcaggact ctacctcata tcagtttgct agcagaaatc   1200
tagaagactg tcagcttcca aacattaatg caatggttaa catcttctgt ctttataatc   1260
tactccttgt aaagactgta gaagaaagcg caacaatcca tctctcaagt agtgtatcac   1320
agtagtagcc tccaggtttc cttaagggac aacatcctta agtcaaaaga gagaagaggc   1380
accactaaaa gatcgcagtt tgcctggtgc agtggctcac acctgtaatc ccaacatttt   1440
gggaacccaa ggtgggtaga tcacgagatc aagagatcaa gaccatagtg accaacatag   1500
tgaaacccca tctctactga aagtgcaaaa attagctggg tgtgttggca catgcctgta   1560
gtcccagcta cttgagaggc tgaggcagga gaatcgtttg aacccgggag gcagaggttg   1620
cagtgtggtg agatcatgcc actacactcc agcctggcga cagagcgaga cttggtttca   1680
aaaaaaaaaa aaaaaaaaaa cttcagtaag tacgtgttat ttttttcaat aaaattctat   1740
tacagtatgt caaaaaaaaa aaaaaaaaa                                     1769
```

<210> SEQ ID NO 6
<211> LENGTH: 281
<212> TYPE: PRT
<213> ORGANISM: HOMO SAPIENS

<400> SEQUENCE: 6

```
Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
```

-continued

```
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 7
<211> LENGTH: 10
<212> TYPE: PRT
<213> ORGANISM: HOMO SAPIENS

<400> SEQUENCE: 7

Ala Leu Ile Thr Gln Gln Asp Leu Ala Pro
 1               5                  10


<210> SEQ ID NO 8
<211> LENGTH: 424
<212> TYPE: PRT
<213> ORGANISM: HOMO SAPIENS

<400> SEQUENCE: 8

Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Ala Ala Pro Gln Gln Lys Arg Ser Ser Pro Ser Glu Gly Leu
```

-continued

```
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr Gln Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Arg Ser Ile Glu Gly Arg Gly Thr
            180                 185                 190

Glu Pro Lys Ser Ala Asp Lys Thr His Thr Cys Pro Pro Cys Pro Ala
        195                 200                 205

Pro Glu Leu Leu Gly Gly Pro Ser Val Phe Leu Phe Pro Pro Lys Pro
    210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Asn Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
    290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Asp Glu Leu Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
    370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
                405                 410                 415

Ser Leu Ser Leu Ser Pro Gly Lys
            420
```

TUMOR NECROSIS FACTOR RELATED RECEPTOR, TR6

This application is a continuation-in-part of U.S. Ser. No. 08/916,625, filed Aug. 22, 1997 which in turn is a continuation-in-part application of U.S. Ser. No: 08/853,684, filed May 9, 1997 now abandoned, which claimed the benefit of U.S. Provisional Application No: 60/041,230, filed Mar. 14, 1997. All three applications are herein incorporated by reference in their entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Tumor Necrosis Factor Related family, hereinafter referred to as TR6. The invention also relates to inhibiting or activating the action of such polynucleotides and polypeptides.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including in host defense processes such as protection against infections, and pathological conditions such as shock responses and inflammatory disease condistions. TNF-X belongs to the "TNF-ligand" superfamily of which 19 members have been identified so far. These ligands mediate their effects through interactions with cell surface or secreted, decoy, receptors, expressed by many different cell types, and which themselves now form a superfamily with 24 indentified members to date.

Among the ligands there are included TNF-α, lymphotoxinα (LT-α, also known as TNF-β), LT-β (found in heterotrimeric complexes, LT-α2-β), FasL, CD40L, CD27L, CD30L, 4-1BBL, OX40L and nerve growth factor (NGF)). The receptor superfamily includes the p55 and p75 TNF receptor, FAS APO-1, CD40, CD27, CD30, 4-1BB, OX40 and the low affinity p75 NGF-receptor (Meager, A., Biologicals, 22:291–295 (1994)).

Many members of the TNF-ligand superfamily are expressed by cells of the immune and hematopoietic system which underscores their role in differentian of the cells of the immune cells and functional responses in host defense mechanisms (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglubulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al, Cell 69:737 (1992)).

TNF-α and LT-α are capable of binding to two TNF receptors (the 55- and 75-kd TNF receptors). A large number of biological effects are elicited by TNF-α and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF-α and LT-α are involved in the pathogenesis of a wide range of diseases, including endotoxic shock, cerebral malaria, tumors, autoimmuine diseases, allergic disorders, AIDS and graft rejection (Beutler, B. and Von Huffel, C., Science 264:667–668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)).

The effects of TNF ligand and TNF receptor families are varied and influence numerous functions, both normal and abnormal, in the biological processes of mammalian and non-mammalian species. There is a clear need, therefore, for identification and characterization of such receptors and ligands that influence biological activity, both normally and in disease states. In particular, there is a need to isolate and characterize novel members of the TNF receptor family.

This indicates that these receptors have an established, proven history as therapeutic targets. Clearly there is a need for identification and characterization of further receptors which can play a role in preventing, ameliorating or correcting dysfunctions or diseases, including, but not limited to, chronic and acute inflammation, arthritis (including rheumatoid arthritis), septicemia, autoimmune diseases (e.g. inflammatory bowel disease, psoriasis), transplant rejection, graft vs. host disease, infection, stroke, ischernia, acute respiratory disease syndrome, asthma, restenosis, brain injury, AIDS, Bone diseases, cancer atheroschlerosis, and Alzheimers disease.

SUMMARY OF THE INVENTION

In one aspect, the invention relates to TR6 polypeptides and recombinant materials and methods for their production. Another aspect of the invention relates to methods for using such TR6 polypeptides and polynucleotides and recombinant materials. Such uses include the treatment of chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer, atheroschlerosis, and Alzheimers disease, among others. Another aspect of the invention relates to methods of using such TR6 polynucleotides, polypeptides and recombinant materials for inhibiting angiogenesis and also inhibiting production of TNF-α and eicosanolds.

In still another aspect, the invention relates to methods to identify agonists and antagonists using the materials provided by the invention, and treating conditions associated with TR6 imbalance with the identified compounds.

Yet another aspect of the invention relates to diagnostic assays for detecting diseases associated with inappropriate TR6 activity or levels.

DESCRIPTION OF THE INVENTION

Definitions

The following definitions are provided to facilitate understanding of certain terms used frequently herein.

"TR6" refers, among others, to a polypeptide comprising the amino acid sequence set forth in SEQ ID NO:2, or an allelic variant thereof.

"Fusion protein" refers to a protein encoded by two, often unrelated, fused genes or fragments thereof. In one example, EP-A-O 464 533 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

In the case of TR6 fusion protein, in one embodiment for example, the fusion protein can be a fusion of the extracellular portion of TR6 fused with the Fc portion of human IgG. In one exemplified construct of SEQ ID NO: 7 of Table 5, extra amino acid residues were introduced within a hinge region between the TR6 and the IgG Fc portions of the molecule to facilitate cleavage of the protein by Factor Xa. This is sometimes desirable to facilitate the enzymatic cleavage of the IgG Fc portion of the recombinant protein from the TR6 part, either to facilitate binding studies or for generation of antibodies selectively to the TR6 portion of the recombinant protein. However, in clinical applications, although it may sometimes be desirable to introduce enzymatic cleavage sites within the recombinant protein, it may not always be desirable to do so. To avoid cleavage of the recombinant protein Factor Xa, it may be desirable to construct a fusion protein of the extracellular portion of TR6 fused directly with the IgG Fc portion.

It may also be desirable to introduce intervening amino acid sequences between the TR6 portion and the IgG Fc portion. Such intervening sequence may sometimes be desirable to modify the in vivo properties of the recombinant protein, such as by making the hinge region more rigid or more flexible. Such residues can also be added or removed to alter the effector function of the the IgG Fc portion of the recombinant protein. Examples of such effector functions include, but are not limited to, complement binding, Fc receptor binding, antibody dependent cellular cytotoxicity.

Other methods to alter the protein of a fusion protein is to use the Fc portions of different immunoglubulin isotypes. Examples of such constructs include, but are not limited to, fusion proteins with portions of IgG1, IgG2, IgG3, IgG4, IgA, IgM. Such constructs are expected to alter the in vivo properties of the recombinant fusion protein. For example, fusion proteins with the Fc portion of IgG4 would be expected to have reduced ability to bind to components of the complement cascade and to have reduced ability to bind to Fc receptor or to mediate ADCC. The Fc portion of IgA is known to facilitate transplacental transport.

Other single or multiple residue mutations can also alter the behaviour and function of such recombinant proteins. For example, single and multipe residue mutations within the Fc portion of immunoglobulins can dramatically alter the Fc effector functions such as reduction in their ability to bind to one or more Fc receptor types. Some outcomes of such changes would be alterations of the pharmacokinetic and pharmacodynamic properties of the recombinant proteins and alterations in the iv vivo consequences such as effects on cells and tissues in vivo. Such alterations may sometimes be desirable in order to improve the clinical utility of the TR6 protein.

Fusion can also be made to the tail portions of proteins such as IgA and IgM which can facilitate expression of multivalent proteins. Other embodiments may include fusion with amino acid sequences which can facility dimer or trimer formation (e.g. zink finger proteins or the stock regions of collagen), heterbifunctional fusion proteins (e.g. with cytokines, immunoglobulin domains or other receptors and ligands) designed to facilitate recognition of more than one target, viral peptide sequences known to mediate protein transduction (e.g. HIV-tat, HSV-VP22), fusion to cytotoxins (e.g. staphyloccocal enterotoxins, ricin). Chemical conjugation of TR6 to cytotoxic, cytostatic or cytoprotective compounds is also possible.

It may also be desirable to alter the glycosylation sites on the recombinant protein to beneficial alter the pharmacokinetic and/or pharrncodynamic properties of the protein or improve manufacturing or stability of the recombinant protein.

"Receptor Activity" or "Biological Activity of the Receptor" refers to the metabolic or physiologic function of said TR6, including similar activities or improved activities or decreased undesirable side-effects of the whole or parts of TR6, including in a recombinatorial form fused with other molecules (e.g. in fusion with parts of immunoglobulins or other desirable polypeptides, such as as TR6-Ig fusion proteins). Also included are antigenic and immunogenic activities of said TR6.

"TR6 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W.H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., cds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12 (1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970) Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970) Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$nn \leq xn-(xn \cdot y),$$

wherein nn is the number of nucleotide alterations, xn is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of xn and y is rounded down to the nearest integer prior to subtracting it from xn. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$na \leq xa-(xa \cdot y),$$

wherein na is the number of amino acid alterations, xa is the total number of amino acids in SEQ ID NO:2, and y is, for instance 0.70 for 70%, 0.80 for 80%, 0.85 for 85% etc., and wherein any non-integer product of xa and y is rounded down to the nearest integer prior to subtracting it from xa.

Polypeptides of the Invention

In one aspect, the present invention relates to TR6 polypeptides. The TR6 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within TR6 polypeptides are polypeptides having the amino acid sequence which have at least 80% identity to the polypeptide having the amino acid sequence of SEQ ID NO:2 over its entire length, and still more preferably at least 90% identity, and even still more preferably at least 95% identity to SEQ ID NO:2. Furthermore, those with at least 97–99% are highly preferred. Preferably TR6 polypeptides exhibit at least one biological activity of the receptor.

The TR6 polypeptides may be in the form of the "mature" protein or may be a part of a larger protein such as a fusion protein. It is often advantageous to include additional amino acid sequences which contain secretory or leader sequences, pro-sequences, sequences which aid in purification such as multiple histidine residues or the Fc portion of immunonoglobulins, which may also improve in vivo half life, or an additional sequence for stability during recombinant production.

The TR6 polypeptides also include fragments of the aforementioned polypeptides. More specifically, a fragment is a polypeptide having an amino acid sequence that entirely is the same as part, but not all, of the amino acid sequence of the aforementioned TR6 polypeptides. An example of fragment is extracellular domain of the polypepitde having the amino acid sequence of SEQ ID NO:2. Amino acid sequence from 1 to 184 is predicted to be the extracellular domain sequence of SEQ ID NO:2, which includes the leader sequence comprising the first 53 amino acids; however, sequences longer or shorter than that of 1 to 184 is also possible for it to be extracellular. As with TR6 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of TR6 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of TR6 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions or soluble forms of the receptor. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO:4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The TR6 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to TR6 polynucleotides. TR6 polynucleotides include isolated polynucleotides which encode the TR6 polypeptides and fragments, and polynucleotides closely related thereto. More specifically, TR6 polynucleotide of the invention include a polynucleotide comprising the nucleotide sequence set forth in SEQ ID NO:1 encoding a TR6 polypeptide of SEQ ID NO:2, and polynucleotides having the particular sequences of SEQ ID NOS:1 and 3. TR6 polynucleotides further include a polynucleotide comprising a nucleotide sequence that has at least 80% identity to a nucleotide sequence encoding the TR6 polypeptide of SEQ ID NO:2 over its entire length, and a polynucleotide that is at least 80% identical to that having SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under TR6 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such TR6 polynucleotides.

TR6 of the invention is structurally related to other proteins of the Tumor Necrosis Factor Receptor family, as shown by the results of sequencing the cDNA encoding human TR6. The cDNA sequence of SEQ ID NO:1 contains an open reading frame (nucleotide numbers 94 to 1329) encoding a polypeptide of 411 amino acids of SEQ ID NO:2. The amino acid sequence of Table 2 (SEQ ID NO:2) has about 58% identity (using GAP (From GCG)) in 411 amino acid residues with DR4, the receptor for the ligand TRAIL. (Pan, G., O'Rourke, K., Chinnaiyan, A. M., Gentz, R., Ebner, R., Ni, J. and Dixit, V. M., Science 276, 111–113 (1997)). The nucleotide sequence of Table 1 (SEQ ID NO:1) has about 70% identity (using GAP (from GCG)) in 1335 nucleotide residues with DR4, the receptor for the ligand TRAIL. TR6 contains a death domain (amino acids 290 to 324 in SEQ ID NO:2) which is 64% identical to the death domain of the human Death receptor 4 (DR4) (Pan, G., O'Rourke, K., Chinnaiyan, A. M., Gentz, R., Ebner, R., Ni, J. and Dixit, V. M., Science 276, 111–113 (1997)), 35.7% identical to the death domain of the human Death receptor 3 (DR3) (A. M. Chinnaiyan, et al, Science 274 (5289), 990–992 (1996)), 32.7% identical to the death domain of human TNFR1, and 19.6% identical to the death domain of CD95 (Fas) (I. Cascino, J. Immunol. 154 (6), 2706–2713 (1995)).

TABLE 1[a]

| | | | | | |
|---|---|---|---|---|---|
| 1 | CTTTGCGCCC | ACAAAATACA | CCGACGATGC | CCGATCTACT | TTAAGGGCTG |
| 51 | AAACCCACGG | GCCTGAGAGA | CTATAAGAGC | GTTCCCTACC | GCCATGGAAC |
| 101 | AACGGGGACA | GAACGCCCCG | GCCGCTTCGG | GGGCCCGGAA | AAGGCACGGC |
| 151 | CCAGGACCCA | GGGAGGCGCG | GGGAGCCAGG | CCTGGGCCCC | GGGTCCCCAA |
| 201 | GACCCTTGTG | CTCGTTGTCG | CCGCGGTCCT | GCTGTTGGTC | TCAGCTGAGT |
| 251 | CTGCTCTGAT | CACCCAACAA | GACCTAGCTC | CCCAGCAGAG | AGCGGCCCCA |
| 301 | CAACAAAAGA | GGTCCAGCCC | CTCAGAGGGA | TTGTGTCCAC | CTGGACACCA |
| 351 | TATCTCAGAA | GACGGTAGAG | ATTGCATCTC | CTGCAAATAT | gGACAGGACT |
| 401 | ATAGCACTCA | ATGGAATGAC | CTCCTTTTCT | GCTTGCGCTG | CACCAGGTGT |
| 451 | GATTCAGGTG | AAGTGGAGCT | AAGTCCCTGC | ACCACGACCA | GAAACACAGT |
| 501 | GTGTCAGTGC | GAAGAAgGCA | CCTTCCGGGA | AGAAGATTCT | CCTGAGATGT |
| 551 | GCCGGAAGTG | CCGCACAGGG | TGTCCCAgAG | GGATGGTCAA | GGTCGGTGAT |
| 601 | TGTACACCCT | GGAGTGACAT | CGAATGTGTC | CACAAAGAAT | CAGGCATCAT |
| 651 | CATAgGAGTC | ACAGTTGCAG | CCGTAGTCTT | GATTGTGGCT | GTGTTTGTTT |
| 701 | GCaAgTCTTT | ACTGTGGAAg | AAAGTCCTTC | CTTACCTGAA | AGGCATCTGC |
| 751 | TCAGGTGGTG | GTGGGGACCC | TGAGCGTGTG | GACAGAAGCT | CACAACGACc |
| 801 | TGGGGCTGAG | GACAATGTCC | TCAATGAGAT | CGTGAGTATC | TTGCAGCCCA |
| 851 | CCCAGGTCCC | TGAGCAGGAA | ATGGAAGTCC | AGGAGCCAGC | AGAGCCAACA |
| 901 | GGTGTCAACA | TGTTGTCCCC | CGGGGAGTCA | GAGCATCTGC | TGGAACCGGC |

TABLE 1[a]-continued

| | |
|---|---|
| 951 | AGAAGCTGAA AGGTCTCAGA GGAGGAGGCT GCTGGTTCCA GCAAATGAAG |
| 1001 | GTGATCCCAC TGAGACTCTG AGACAGTGCT TCGATGACTT TGCAGACTTG |
| 1051 | GTGCCCTTTG ACTCCTGGGA gCCgCTCATG AGGAAGTTGG GCCTCATGGA |
| 1101 | CAATgAGATa aaGGTGGCTA AAGCTGAGGC AGCGGGCCAC AGGGACACCT |
| 1151 | TGTACACGAT GCTGATAAAG TGGGTCAACA AAACCGGGCG AGATGCCTCT |
| 1201 | GTCCACACCC TGCTGGATGC CTTGGAGACG CTGGGAGAGA GACTTGCCAA |
| 1251 | GCAGAAGATT GAGGACCACT TGTTGAGCTC TGGAAAGTTC ATGTATCTAG |
| 1301 | AAGGTAATGC AGACTCTGCC ATGTCCTAAG TGTGATTCTC TTCAGGAAGT |
| 1351 | CAGACCTTCC CTGGTTTACC TTTTTTCTGG AAAAAGCCCA ACTGGACTCC |
| 1401 | AGTCAGTAGG AAAGTGCCAC AATTGTCACA TGACCGGTAC TGGAAGAAAC |
| 1451 | TCTCCCATCC AACATCACCC AGTGGATGGA ACATCCTGTA ACTTTTCACT |
| 1501 | GCACTTGGCA TTATTTTTAT AAGCTGAATG TGATAATAAG GACACTATGG |
| 1551 | AAATGTCTGG ATCATTCCGT TTGTGCGTAC TTTGAgATTT GGTTTGGGAT |
| 1601 | GTCATTGTTT TCACAGCACT TTTTTATCCT AATGTAAATG CTTTATTTAT |
| 1651 | TTATTTGGGC TACATTGTAA gATCCATCTA CACAGTCGTT GTCCGACTTC |
| 1701 | ACTTGATACT ATATGATATG AACCTTTTTT GGGTGGGGGG TGCGGGGCAg |
| 1751 | TTCACTCTGT CTCCCAGGCT GGAGTGCAAT GGTGCAATCT TGGCTCACTA |
| 1801 | TAGCCTTGAC CTCTCAGGCT CAAGCGATTC TCCCACCTCA GCCATCCAAA |
| 1851 | TAGCTGGGAC CACAGGTGTG CACCACCACG CCCGGCTAAT TTTTTGTATT |
| 1901 | TTGTCTAgAT ATAGGGGCTC TCTATGTTGC TCAGGGTGGT CTCgAATTCC |
| 1951 | TGGACTCAAG CAGTCTGCCC ACCTCAGACT CCCAAAGCGG TGGAATTAGA |
| 2001 | GGCGTGAGCC CCCATGCTTG gCCTTACcTT TCTACTTTTA TAATTCTGTA |
| 2051 | TGTTATTATT TTATGAACAT GAAGAAACTT TAGTAAATGT ACTTGTTTAC |
| 2101 | ATAGTTATGT GAATAGATTA GATAAACATA AAAGGAGGAG ACATACAATG |
| 2151 | GGGGAAGAAG AAGAAGTCCC CTGTAAGATG TCACTGTcTG GGTTCCAGCC |
| 2201 | CTCCCTCAGA TGTACTTTGG CTTCAATGAT TGGCAACTTC TACAGGGGCC |
| 2251 | AGTCTTTTGA ACTGGACAAC CTTACAAGTA TATGAGTATT ATTTATAGGT |
| 2301 | AGTTGTTTAC ATATGAGTCG GGACCAAAGA GAACTGGATC CACGTGAAGT |
| 2351 | CCTGTGTGTG GCTGGTCCCT ACCTGGGCAG TcTCATTTGC ACCCATAGCC |
| 2401 | CCCATCTATG GACAGGCTGG GACAGAGGCA GATGGGTTAG ATCACACATA |
| 2451 | ACAATAGGGT CTATGTCATA TCCCAAGTGA ACTTGAGCCC TGTTTGGGCT |
| 2501 | CAGGAGATAG AAGACAAAAT CTGTCTCCCC ACGTCTGCCA TGGCATCAAG |
| 2551 | GGGGAAGAGT AGATGGTGCT tGAGAATGGT GTGAAATGGT TGCCATCTCA |
| 2601 | GGAGTAGATG GCCCGGCTCA CTTCTGGTTA TCtGTCACCC TGAGCCCAtG |
| 2651 | AGCTGCcTTT TAGGGTACAG ATTGCCTACT TGAGGACCTT GGCCGCTCTG |
| 2701 | TAAGCATCTG ACTCATCTCA GAAATGTCAA TTCTTAAACA CTGTGGCAAC |
| 2751 | AGGACCTAGA ATGGCTGACG CATTAAGGTT TTCTTcTTGT GTCCTGTTCT |
| 2801 | ATTAtTGTTT TAAGACCTCA GTAACCATTT CAGCCTCTTT CCAGCAAACC |
| 2851 | CTTCTCCATA GTATTTCAGT CATGGAAGGA TCATTTATGC AGGTAGTCAT |

TABLE 1[a]-continued

| | | | | | |
|---|---|---|---|---|---|
| 2901 | TCCAGGAGTT | TTTGGTCTTT | TCTGTCTCAA | GGCATTGTGT | GTTTTGTTCC |
| 2951 | GGGACTGGTT | TGGGTGGGAC | AAAGTTAGAA | TTGCCTGAAG | ATcAcACATT |
| 3001 | CAGACTGTtG | TGTCTGTGGA | GTTTTAGGAG | TGGGGGGTGA | CCTTTcTGGT |
| 3051 | CTTtGcAcTT | CCATCcTcTC | CCAcTTCCAT | cTGGCATCCC | CACGcGTTGT |
| 3101 | CCCcTGCAcT | TcTGGAAGGC | ACAGGGTGCT | GCTGCTTCCT | GGTCTTTGCC |
| 3151 | TTTGCTGGGC | cTTCTGTGCA | GGACGCTCAG | CCTCAGGGCT | CAGAAGGTGC |
| 3201 | CAGTCCGGTC | CCAGGTCCCT | TGTCCCTTCC | ACAGAGGCCT | TCcTAGAAGA |
| 3251 | TGCATCTAGA | GTGTCAGCCT | TATCAGTGTT | TAAGATTTTT | CTTTTATTTT |
| 3301 | TAATTTTTTT | GAGACAGAAT | CTCACTCTCT | CGCCCAGGCT | GGAGTGCAAC |
| 3351 | GGTACGATCT | TGGCTCAGTG | CAACCTCCGC | CTCCTGGGTT | CAAGCGATTC |
| 3401 | TCGTGCCTCA | GCCTCCGGAG | TAGCTGGGAT | TGCAGGCACC | CGCCACCACG |
| 3451 | CCTGGCTAAT | TTTTGTATTT | TTAGTAGAGA | CGGGGTTTCA | CCATGTTGGT |
| 3501 | CAGGCTGGTC | TCGAACTCCT | GACCTCAGGT | GATCCACNTT | GGCCTCCGAA |
| 3551 | AGTGCTGGGa | tatacaaggc | GTGAGCCACC | AGCCAGGCCA | AGATATTNTT |
| 3601 | NTAAAGNNAG | CTTCCGGANG | ACATGAAATA | ANGGGGGGTT | TTGTTGTTTA |
| 3651 | GTAACATTNG | GCTTTGATAT | ATCCCCAGGC | CAAATNGCAN | GNGACACAGG |
| 3701 | ACAGCCATAG | TATAGTGTGT | CACTCGTGGT | TGGTGTCCTT | TCATGGTTCT |
| 3751 | GCCCTGTCAA | AGGTCCCTAT | TTGAAATGTG | TTATAATACA | AACAAGGAAG |
| 3801 | CACATTGTGT | ACAAAATACT | TATGTATTTA | TGAATCCATG | ACCAAATTAA |
| 3851 | ATATGAAACC | TTATATAAAA | AAAAAAAAAA | A | |

[a]A nucleotide sequence of a human TR6. (SEQ ID NO: 1).

TABLE 2[b]

| | | | | | | | | | | | | | | | | |
|---|---|---|---|---|---|---|---|---|---|---|---|---|---|---|---|---|
| 1 | Met | Glu | Gln | Arg | Gly | Gln | Asn | Ala | Pro | Ala | Ala | Ser | Gly | Ala | Arg | Lys 16 |
| 17 | Arg | His | Gly | Pro | Gly | Pro | Arg | Glu | Ala | Arg | Gly | Ala | Arg | Pro | Gly | Pro 32 |
| 33 | Arg | Val | Pro | Lys | Thr | Leu | Val | Leu | Val | Val | Ala | Ala | Val | Leu | Leu | Leu 48 |
| 49 | Val | Ser | Ala | Glu | Ser | Ale | Leu | Ile | Thr | Gln | Gln | Asp | Leu | Ala | Pro | Gln 64 |
| 65 | Gln | Arg | Ala | Ala | Pro | Gln | Gln | Lys | Arg | Ser | Ser | Pro | Ser | Glu | Gly | Leu 80 |
| 81 | Cys | Pro | Pro | Gly | His | His | Ile | Ser | Glu | Asp | Gly | Arg | Asp | Cys | Ile | Ser 96 |
| 97 | Cys | Lys | Tyr | Gly | Gln | Asp | Tyr | Ser | Thr | Gln | Trp | Asn | Asp | Leu | Leu | Phe 112 |
| 113 | Cys | Leu | Arg | Cys | Thr | Arg | Cys | Asp | Ser | Gly | Glu | Val | Glu | Leu | Ser | Pro 128 |
| 129 | Cys | Thr | Thr | Thr | Arg | Asn | Thr | Val | Cys | Gln | Cys | Glu | Glu | Gly | Thr | Phe 144 |
| 145 | Arg | Glu | Glu | Asp | Ser | Pro | Glu | Met | Cys | Arg | Lys | Cys | Arg | Thr | Gly | Cys 160 |
| 161 | Pro | Arg | Gly | Met | Val | Lys | Val | Gly | Asp | Cys | Thr | Pro | Trp | Ser | Asp | Ile 176 |
| 177 | Glu | Cys | Val | His | Lys | Glu | Ser | Gly | Ile | Ile | Ile | Gly | Val | Thr | Val | Ala 192 |
| 193 | Ala | Val | Val | Leu | Ile | Val | Ala | Val | Phe | Vai | Cys | Lys | Ser | Leu | Leu | Trp 208 |
| 209 | Lys | Lys | Val | Leu | Pro | Tyr | Leu | Lys | Gly | Ile | Cys | Ser | Gly | Gly | Gly | Gly 224 |
| 225 | Asp | Pro | Glu | Arg | Val | Asp | Arg | Ser | Ser | Gln | Arg | Pro | Gly | Ala | Glu | Asp 240 |
| 241 | Asn | Val | Leu | Asn | Glu | Ile | Val | Ser | Ile | Leu | Gln | Pro | Thr | Gln | Val | Pro 256 |
| 257 | Glu | Gln | Glu | Met | Glu | Val | Gln | Glu | Pro | Ala | Glu | Pro | Thr | Gly | Val | Asn 272 |

TABLE 2[b]-continued

| | | | | | | | | | | | | | | | | | |
|---|---|---|---|---|---|---|---|---|---|---|---|---|---|---|---|---|---|
| 273 | Met | Leu | Ser | Pro | Gly | Glu | Ser | Glu | His | Leu | Leu | Glu | Pro | Ala | Glu | Ala | 288 |
| 289 | Glu | Arg | Ser | Gln | Arg | Arg | Arg | Leu | Leu | Val | Pro | Ala | Asn | Glu | Gly | Asp | 304 |
| 305 | Pro | Thr | Glu | Thr | Leu | Arg | Gln | Cys | Phe | Asp | Asp | Phe | Ala | Asp | Leu | Val | 320 |
| 321 | Pro | Phe | Asp | Ser | Trp | Glu | Pro | Leu | Met | Arg | Lys | Leu | Gly | Leu | Met | Asp | 336 |
| 337 | Asn | Glu | Ile | Lys | Val | Ala | Lys | Ala | Glu | Ala | Ala | Gly | His | Arg | Asp | Thr | 352 |
| 353 | Leu | Tyr | Thr | Met | Leu | Ile | Lys | Trp | Val | Asn | Lys | Thr | Gly | Arg | Asp | Ala | 368 |
| 369 | Ser | Val | His | Thr | Leu | Leu | Asp | Ala | Leu | Glu | Thr | Leu | Gly | Glu | Arg | Leu | 384 |
| 385 | Ala | Lys | Gln | Lys | Ile | Glu | Asp | His | Leu | Leu | Ser | Ser | Gly | Lys | Phe | Met | 400 |
| 401 | Tyr | Leu | Glu | Gly | Asn | Ala | Asp | Ser | Ala | Met | Ser | End | | | | | 411 |

[b]An amino acid sequence of a human TR6. (SEQ ID NO: 2).

One polynucleotide of the present invention encoding TR6 may be obtained using standard cloning and screening, from a cDNA library derived from mRNA in cells of human thymus stromal cells, monocytes, peripheral blood lymphocytes, primary dendritic, and bone marrow cells using the expressed sequence tag (EST) analysis (Adams, M. D., et al. *Science* (1991) 252:1651–1656; Adams, M. D. etal., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding TR6 polypeptide of SEQ ID NO:2 may be identical to the polypeptide encoding sequence contained in Table 1 (nucleotide number 94 to 1329 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of TR6 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding TR6 variants comprising the amino acid sequence of TR6 polypeptide of Table 1 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO:3) encoding the amino acid sequence of Table 4 (SEQ ID NO:4).

TABLE 3[c]

| | | | | | |
|---|---|---|---|---|---|
| 1 | ATGACCTCCT | TTTCTGCTTG | CGCTGCACCA | GGTGTGATTC | AGGTGAAGTG |
| 51 | GAGCTAAGTC | CCTGCACCAC | GACCAGAAAC | ACAGTGTGTC | AGTGCGAAGA |
| 101 | AgGCACCTTC | CGGGAAGAAG | ATTCTCCTGA | GATGTGCCGG | AAGTGCCGCA |
| 151 | CAGGGTGTCC | CAgAGGGATG | GTCAAGGTCG | GTGATTGTAC | ACCCTGGAGT |
| 201 | GACATCGAAT | GTGTCCACAA | AGAATCAGGC | ATCATCATAg | GAGTCACAGT |
| 251 | TGCAGCCGTA | GTCTTGATTG | TGGCTGTGTT | TGTTTGCaAg | TCTTTACTGT |
| 301 | GGAAgAAAGT | CCTTCCTTAC | CTGAAAGGCA | TCTGCTCAGG | TGGTGGTGGG |
| 351 | GACCCTGAGC | GTGTGGACAG | AAGcTCACAA | CGACcTGGGG | CTGAGGACAA |
| 401 | TGTCCTCAAT | GAGATCGTGA | GTATCTTGCA | GCCCACCCAG | GTCCCTGAGC |
| 451 | AGGAAATGGA | AGTCCAGGAG | CCAGCAGAGC | CAACAGGTGT | CAACATGTTG |
| 501 | TCCCCCGGGG | AGTCAGAGCA | TCTGCTGGAA | CCGGCAGAAG | CTGAAAGGTC |
| 551 | TCAGAGGAGG | AGGCTGCTGG | TTCCAGCAAA | TGAAGGTGAT | CCCACTGAGA |
| 601 | CTCTGAGACA | GTGCTTCGAT | GACTTTGCAG | ACTTGGTGCC | CTTTGACTCC |

TABLE 3[c]-continued

| | | | | | |
|---|---|---|---|---|---|
| 651 | TGGGAgCCgC | TCATGAGGAA | GTTGGGCCTC | ATGGACAATg | AGATaaaGGT |
| 701 | GGCTAAAGCT | GAGGCAGCGG | GCCACAGGGA | CACCTTGTAC | ACGATGCTGA |
| 751 | TAAAGTGGGT | CAACAAAACC | GGGCGAGATG | CCTCTGTCQA | CACCCTGCTG |
| 801 | GATGCCTTGG | AGACGCTGGG | AGAGAGACTT | GCCAAGCAGA | AGATTGAGGA |
| 851 | CCACTTGTTG | AGCTCTGGAA | AGTTCATGTA | TCTAGAAGGT | AATGCAGACT |
| 901 | CTGCCATGTC | CTAAGTGTGA | TTCTCTTCAG | GAAGTCAGAC | CTTCCCTGGT |
| 951 | TTACCTTTTT | TCTGGAAAAA | GCCCAACTGG | ACTCCAGTCA | GTAGGAAAGT |
| 1001 | GCCACAATTG | TCACATGACC | GGTACTGGAA | GAAACTCTCC | CATCCAACAT |
| 1051 | CACCCAGTGG | AT | | | |

[c]A partial nucleotide sequence of a human TR6. (SEQ ID NO: 3).

TABLE 4[d]

| | | | | | |
|---|---|---|---|---|---|
| 1 | DLLFCLRCTR | CDSGEVELSP | CTTTRNTVCQ | CEEGTFREED | SPENCRKCRT |
| 51 | GCPRGMVKVG | DCTPWSDIEC | VHKESGIIIG | VTVAAVVLIV | AVFVCKSLLW |
| 101 | KKVLPYLKGI | CSGGGGDPER | VDRSSQRPGA | EDNVLNEIVS | ILQPTQVPEQ |
| 151 | EMEVQEPAEP | TGVNMLSPGE | SEHLLEPAEA | ERSQRRRLLV | PANEGDPTET |
| 201 | LRQCFDDFAD | LVPFDSWEPL | NRKLGLMDNE | IKVAKAEAAG | HRDTLYTMLI |
| 251 | KWVNKTGRDA | SVHTLLDALE | TLGERLAKQK | IEDHLLSSGK | FNYLEGNADS |
| 301 | AMS* | | | | |

[d]A partial amino acid sequence of a human TR6. (SEQ ID NO: 4).

TABLE 5

(SEQ ID NO: 7)

| | | | | | |
|---|---|---|---|---|---|
| 1 | MEQRGQNAPAASGARKRHGPGPREARGARPGPRVPKTLVLVVAAVLLLVS | | | | |
| 51 | AESALITQQDLAPQQRAAPQQKRSSPSEGLCPPQKHISEDQRDCISCKYQ | | | | |
| 101 | QDYSTQWNDLLFCLRCTRCDSGEVELSPCTTTRNTVCQCEEQTFREEDSP | | | | |
| 151 | EMCRKCRTQCPRQMVKVQDCTPWSDIECVHKESGRSIEGR | GTEPKSADKT | | | |
| 201 | HTCPPCPAPE | LLGGPSVFLF | PPKPKDTLMI | SRTPEVTCVV | VDVSHEDPEV |
| 251 | KFNWYVDGVE | VHNAKTKPRE | EQYNSTYRVV | SVLTVLHQDW | LNGKEYKCKV |
| 301 | SNKALPAPIE | KTISKAKGQP | REPQVYTLPP | SRDELTKNQV | SLTCLVKGFY |
| 351 | PSDIAVEWES | NGQPENNYKT | TPPVLDSDGS | FFLYSKLTVD | KSRWQQGNVF |
| 401 | SCSVMHEALH | NHYTQKSLSL | SPGK* | | |

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences. occur only if there is at least 95% and preferably at least 97% identity between the sequences.

Polynucleotides of the invention, which are identical or sufficiently identical to a nucleotide sequence contained in SEQ ID NO:1 or a fragment thereof, including that of SEQ ID NO:3, may be used as hybridization probes for cDNA and genomic DNA, to isolate full-length cDNAs and genomic clones encoding TR6 and to isolate cDNA and genomic clones of other genes that have a high sequence similarity to the TR6 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding TR6 polypeptide comprises the steps of screening an appropriate library under stringent hybridization conditions with a labeled probe having the SEQ ID NO:1 or a fragment thereof, including that of SEQ ID NO:3, and isolating full-length cDNA and genomic clones containing said polynucleotide sequence. Such hybridization techniques are well known to those of skill in the art. Thus in another aspect, TR6 polynucleotides of the present invention further include a nucleotide sequence comprising a nucleotide sequence that hybridize under stringent condition to a nucleotide sequence having SEQ ID NO:1 or a fragment thereof, including that of SEQ ID NO:3. Also included with TR6 polypeptides are polypeptide comprising amino acid sequence encoded by nucleotide sequence obtained by the above hybridization condition. Stringent hybridization conditions are as defined above or alternatively conditions under overnight incubation at 42° C. in a solution comprising: 50% formamide, 5×SSC (150rnM NaCl, 15mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the TR6 polypeptide is to be expressed for use in screening assays, generally, it is preferred that the polypeptide be produced at the surface of the cell. In this event, the cells may be harvested prior to use in the screening assay. If TR6 polypeptide is secreted into the medium, the medium can be recovered in order to recover and purify the polypeptide; if produced intracellularly, the cells must first be lysed before the polypeptide is recovered.

TR6 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of TR6 polynucleotides for use as diagnostic reagents. Detection of a mutated form of TR6 gene associated with a dysfunction will provide a diagnostic tool that can add to or define a diagnosis of a disease or susceptibility to a disease which results from under-expression, over-expression or altered expression of TR6. Individuals carrying mutations in the TR6 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled TR6 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S I protection or the chemical cleavage method. See Cotton et al., *Proc Natl Acad Sci USA* (1985) 85: 4397–4401. In another embodiment, an array of oligonucleotides probes comprising TR6 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others. through detection of mutation in the TR6 gene by the methods described.

In addition, chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others., can be diagnosed by methods comprising determining from a sample derived from a subject an abnormally decreased or increased level of TR6 polypeptide or TR6 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an TR6, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

The 3' untranslated region of TR6 matches the 295 bp nucleotide sequence of a mapped EST (Genbank ID: D20151). This EST has been mapped by the Whitehead Institute to chromosome 8, 97.68 cR from the top of the Chromosome 8 linkage group

Antibodies

The polypeptides of the invention or their fragments or analogs thereof, or cells expressing them can also be used as immunogens to produce antibodies immunospecific for the TR6 polypeptides. The term "immunospecific" means that the antibodies have substantiall greater affinity for the polypeptides of the invention than their affinity for other related polypeptides in the prior art.

Antibodies generated against the TR6 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against TR6 polypeptides may also be employed to treat chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others., among others.

Vaccines

Another aspect of the invention relates to a method for inducing an immunological response in a mammal which comprises inoculating the mammal with TR6 polypeptide, or a fragment thereof, adequate to produce antibody and/or T cell immune response to protect said animal from chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others. Yet another aspect of the invention relates to a method of inducing immunological response in a mammal which comprises, delivering TR6 polypeptide via a vector directing expression of TR6 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a TR6 polypeptide wherein the composition comprises a TR6 polypeptide or TR6 gene. The vaccine formulation may further comprise a suitable carrier. Since TR6 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

We have now discovered that TL2 of SEQ ID NO:6 (otherwise known as TRAL, Immunity (6):673–682 (1995)) is a ligand of TR6. Thus, the TR6 polypeptide of the present invention, and one of its ligands, TL2 may be employed in a screening process for compounds which bind the receptor, or its ligand, and which activate (agonists) or inhibit activation of (antagonists) the receptor polypeptide of the present invention, or its ligand TL2. Thus, polypeptides of the invention may be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

TR6 polypeptides are responsible for many biological functions, including many pathologies. Accordingly, it is desirous to find compounds and drugs which stimulate TR6 on the one hand and which can inhibit the function of TR6 or remove TR6 expressing cells on the other hand. Antagonists, or agents which remove TR6 expressing cells, may be employed for a variety of therapeutic and prophylactic purposes for such conditions as chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others. Agonists can be employed for therapeutic and prophylactic purposes for such conditions responsive to activation of T cells and other components of the immune system, such as for treatment of cancer and AIDS. However, agonists can also be employed for inappropriate stimulation of T cells and other components of the immune system which leads to down modulation of immnune activity with therapeutic or prophylactic application for conditions such , as chronic and acute inflammation, arthritis (including rheumatoid arthritis), septicemia, autoimmune diseases (e.g. inflammatory bowel disease, psoriasis), transplant rejection, graft vs. host disease, infection, stroke, ischemia, acute respiratory disease syndrome, asthma, restenosis, brain injury, AIDS, Bone diseases, cancer (e.g. lymphoproliferative disorders), atheroschlerosis, and Alzheimers disease, among others. Candidate compounds may be identified using assays to detect compounds which inhibit binding of TL2 to TR6 in either cell-free or cell based assays. Suitable cell-free assays may be readily determined by one of skill in the art. For example, an ELISA format may be used in which purified TR6, or a purified derivative of TR6, containing the extracellular domain of TR6, is immobilized on a suitable surface, either directly or indirectly (e.g., via an antibody to TR6) and candidate compounds are identified by their ability to block binding of purified TL2 to TR6. The binding of TL2 to TR6 could be detected by using a label directly or indirectly associated with TL2. Suitable detection systems include the streptavidin horseradish peroxidase conjugate, or direct conjugation by a tag, e.g., fluorescein. Conversely, purified TL2 may be immobilized on a suitable surface, and candidate compounds identified by their ability to block binding of purified TR6 to TL2. The binding of TR6 to TL2 could be detected by using a label directly or indirectly associated with TR6. Many other assay formats are possible that use the TR6 protein and its ligands.

Suitable cell based assays may be readily determined by one of skill in the art. In general, such screening procedures involve producing appropriate cells which express the receptor polypeptide of the present invention on the surface thereof. Such cells include cells from mammals, yeast, Drosophila or *E. coli*. Cells expressing the receptor (or cell membrane containing the expressed receptor) are then contacted with a known ligand, such as TL2, or test compound to observe binding, or stimulation or inhibition of a functional response. The assays may simply test binding of a candidate compound wherein adherence to the cells bearing the receptor is detected by means of a label directly or indirectly associated with the candidate compound or in an assay involving competition with a labeled competitor, such as the ligand TL2. Further, these assays may test whether the candidate compound results in a signal generated by activation of the receptor or its ligand (e.g. TL2)using detection systems appropriate to the cells bearing the receptor or its ligand and fusion proteins thereof at their surfaces. Typical fusion partners include fusing the extracellular domain of the receptor or ligand with the intracellular tyrosine kinase domain of a second receptor. Inhibitors of activation are generally assayed in the presence of a known agonist, such as the ligand TL2, and the effect on activation by the agonist by the presence of the candidate compound is observed. Standard methods for conducting such screening assays are well understood in the art.

Examples of potential TR6 antagonists include antibodies or, in some cases, oligonucleotides or proteins which are closely related to the ligand of the TR6, e.g., a fragment of the ligand TL2, or small molecules which bind to the receptor, or its ligand, but do not elicit a response, so that the activity of the receptor is prevented. Examples of potential TR6 agonists include antibodies that bind to TR6, its ligand, such as TL2, or derivatives thereof, and small molecules that bind to TR6. These agonists will elicit a response mimicking all or part of the response induced by contacting the native ligand.

The nucleotide sequence of TL2 (SEQ ID NO:5) (published by Immunex Research and Development Corporation, Seattle, Washington as TNF-related apoptosis-inducing ligand (TRAIL) TWiley SR, et al. *Immunity* (6):673–682 (1995)) is as follows.

```
   1 CCTCACTGAC TATAAAAGAA TAGAGAAGGA AGGGCTTCAG TGACCGGCTG
  51 CCTGGCTGAC TTACAGCAGT CAGACTCTGA CAGGATCATG GCTATGATGG
 101 AGGTCCAGGG GGGACCCAGC CTGGGACAGA CCTGCGTGCT GATCGTGATC
 151 TTCACAGTGC TCCTGCAGTC TCTCTGTGTG GCTGTAACTT ACGTGTACTT
 201 TACCAACGAG CTGAAGCAGA TGCAGGACAA GTACTCCAAA AGTGGCATTG
 251 CTTGTTTCTT AAAAGAAGAT GACAGTTATT GGGACCCCAA TGACGAAGAG
 301 AGTATGAACA GCCCCTGCTG GCAAGTCAAG TGGCAACTCC GTCAGCTCGT
 351 TAGAAAGATG ATTTTGAGAA CCTCTGAGGA AACCATTTCT ACAGTTCAAG
 401 AAAAGCAACA AAATATTTCT CCCCTAGTGA GAGAAAGAGG TCCTCAGAGA
 451 GTAGCAGCTC ACATAACTGG GACCAGAGGA AGAAGCAACA CATTGTCTTC
 501 TCCAAACTCC AAGAATGAAA AGGCTCTGGG CCGCAAAATA AACTCCTGGG
 551 AATCATCAAG GAGTGGGCAT TCATTCCTGA GCAACTTGCA CTTGAGGAAT
 601 GGTGAACTGG TCATCCATGA AAAAGGGTTT TACTACATCT ATTCCCAAAC
 651 ATACTTTCGA TTTCAGGAGG AAATAAAAGA AAACACAAAG AACGACAAAC
 701 AAATGGTCCA ATATATTTAC AAATACACAA GTTATCCTGA CCCTATATTG
 751 TTGATGAAAA GTGCTAGAAA TAGTTGTTGG TCTAAAGATG CAGAATATGG
 801 ACTCTATTCC ATCTATCAAG GGGGAATATT TGAGCTTAAG GAAAATGACA
 851 GAATTTTTGT TTCTGTAACA AATGAGCACT TGATAGACAT GGACCATGAA
 901 GCCAGTTTTT TCGGGGCCTT TTTAGTTGGC TAACTGACCT GGAAAGAAAA
 951 AGCAATAACC TCAAAGTGAC TATTCAGTTT TCAGGATGAT ACACTATGAA
1001 GATGTTTCAA AAAATCTGAC CAAAACAAAC AAACAGAAAA CAGAAAACAA
1051 AAAAACCTCT ATGCAATCTG AGTAGAGCAG CCACAACCAA AAAATTCTAC
1101 AACACACACT GTTCTGAAAG TGACTCACTT ATCCCAAGAA AATGAAATTG
1151 CTGAAAGATC TTTCAGGACT CTACCTCATA TCAGTTTGCT AGCAGAAATC
1201 TAGAAGACTG TCAGCTTCCA AACATTAATG CAATGGTTAA CATCTTCTGT
1251 CTTTATAATC TACTCCTTGT AAAGACTGTA GAAGAAAGCG CAACAATCCA
1301 TCTCTCAAGT AGTGTATCAC AGTAGTAGCC TCCAGGTTTC CTTAAGGGAC
1351 AACATCCTTA AGTCAAAAGA GAGAAGAGGC ACCACTAAAA GATCGCAGTT
1401 TGCCTGGTGC AGTGGCTCAC ACCTGTAATC CCAACATTTT GGGAACCCAA
1451 GGTGGGTAGA TCACGAGATC AAGAGATCAA GACCATAGTG ACCAACATAG
1501 TGAAACCCCA TCTCTACTGA AAGTGCAAAA ATTAGCTGGG TGTGTTGGCA
1551 CATGCCTGTA GTCCCAGCTA CTTGAGAGGC TGAGGCAGGA GAATCGTTTG
1601 AACCCGGGAG GCAGAGGTTG CAGTGTGGTG AGATCATGCC ACTACACTCC
1651 AGCCTGGCGA CAGAGCGAGA CTTGGTTTCA AAAAAAAAAA AAAAAAAAAA
1701 CTTCAGTAAG TACGTGTTAT TTTTTTCAAT AAAATTCTAT TACAGTATGT
1751 CAAAA AAAA
```

The amino acid sequence of TL2 (SEQ ID NO:6) (published by Immunex Research and Development Corporation, Seattle, Wash. as TNF-related apoptosis-inducing ligand (TRAIL) TWiley SR, et al. *Immunity* (6):673–682 (1995)) is as follows:

```
  1 Met Ala Met Met Glu Val Gln Gly Gly Pro Ser Leu Cly Gln Thr Cys 16

 17 Val Leu Ile Val Ile Phe Thr Val Leu Leu Gln Ser Leu Cys Val Ala 32

 33 Val Thr Tyr Val Tyr Phe Thr Asn Glu Leu Lys Gln Met Gln Asp Lys 48

 49 Tyr Ser Lys Ser Gly Ile Ala Cys Phe Leu Lys Glu Asp Asp Ser Tyr 64

 65 Trp Asp Pro Asn Asp Glu Glu Ser Met Asn Ser Pro Cys Trp Gln Val 80

 81 Lys Trp Gln Leu Arg Gln Leu Val Arg Lys Met Ile Leu Arg Thr Ser 96

 97 Glu Glu Thr Ile Ser Thr Val Gln Glu Lys Gln Gln Asn Ile Ser Pro 112

113 Leu Val Arg Glu Arg Gly Pro Gln Arg Val Ala Ala His Ile Thr Gly 128

129 Thr Arg Gly Arg Ser Asn Thr Leu Ser Ser Pro Asn Ser Lys Asn Glu 144

145 Lys Ala Leu Gly Arg Lys Ile Asn Ser Trp Glu Ser Ser Arg Ser Gly 160

161 His Ser Phe Leu Ser Asn Leu His Leu Arg Asn Gly Glu Leu Val Ile 176

177 His Glu Lys Gly Phe Tyr Tyr Ile Tyr Ser Gln Thr Tyr Phe Arg Phe 192

193 Gln Glu Glu Ile Lys Glu Asn Thr Lys Asn Asp Lys Gln Met Val Gln 208

209 Tyr Ile Tyr Lys Tyr Thr Ser Tyr Pro Asp Pro Ile Leu Leu Met Lys 224

225 Ser Ala Arg Asn Ser Cys Trp Ser Lys Asp Ala Glu Tyr Gly Leu Tyr 240

241 Ser Ile Tyr Gln Gly Gly Ile Phe Glu Leu Lys Glu Asn Asp Arg Ile 256

257 Phe Val Ser Val Thr Asn Glu His Leu Ile Asp Met Asp His Glu Ala 272

273 Ser Phe Phe Gly Ala Phe Leu Val Gly End                         281
```

Prophylactic and Therapeutic Methods

This invention provides methods of treating abnormal conditions such as, chronic and acute inflammation, arthritis, septicemia, autoimmune diseases (e.g. inflammatory bowel disease, psoriasis, rheumatoid arthritis), transplant rejection, graft vs. host disease, infection, stroke, ischemia, congestive heart failure, restenosis, acute respiratory disease syndrome, asthma, restenosis, brain injury, AIDS, Bone diseases, cancer (e.g. lymphoproliferative disorders), atheroschlerosis, and Alzheimers disease, among others, related to both an excess of or insufficient amounts of TR6 activity.

Another aspect of the invention relates to methods of using such TR6 polypeptides and polynucleotides for inhibiting angiogenesis and also inhibiting production of TNF-α and eicosanoids thereof expressing a TR6 polypeptide. In one preferred embodiment, the present invention contemplates a method of inhibiting angiogenesis in an individual in need thereof comprising administering extracellular domain of TR6 or soluble TR6 fusion protein to the individual. In yet another embodiment, the present invention also relates to a method of lowering the production of eicosanoid or TNF-α in an individual in need thereof comprising administering extracellular domain of TR6 or soluble TR6 fusion protein to the individual.

If the activity of TR6 is in excess, several approaches are available. One approach comprises administering to a subject an inhibitor compound (antagonist) as hereinabove described along with a pharmaceutically acceptable carrier in an amount effective to inhibit activation by blocking binding of ligands to the TR6, or by inhibiting a second signal, and thereby alleviating the abnormal condition. In another approach, soluble forms of TR6 polypeptides still capable of binding the ligand in competition with endogenous TR6 may be administered. Typical embodiments of such competitors comprise fragments of the TR6 polypeptide.

In still another approach, expression of the gene encoding endogenous TR6 can be inhibited using expression blocking techniques. Known such techniques involve the use of antisense sequences, either internally generated or separately administered. See, for example, O'Connor, J Neurochem (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan etal., *Science* (1991) 251:1360. These oligomers can be administered per se or the relevant oligomers can be expressed in vivo.

For treating abnormal conditions related to an under-expression of TR6 and its activity, several approaches are also available. One approach comprises administering to a subject a therapeutically effective amount of TR6 polypeptides or a compound which activates TR6, i.e., an agonist as described above, in combination with a pharmaceutically acceptable carrier, to thereby alleviate the abnormal condition. Alternatively, gene therapy may be employed to effect the endogenous production of TR6 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of TR6 polypeptides in combination with a suitable pharmaceutical carrier.

Formulation and Administration

Peptides, such as the soluble form of TR6 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Two ESTs (EST#1760054 and EST#1635744) with sequence similarity to the human TNF receptor were discovered in a commercial EST database. Analysis of the two nucleotide sequences (3,466 bp and 2,641 bp respectively), revealed each was a partial sequence of the complete cDNA sequence, overlapping, with 100% identity, 2,226 bp at the nucleotide level. Together, the two sequences encompassed the complete predicted cDNA sequence of 3,881 bp, and encoded an open reading frame for a novel member of the TNF receptor superfamily and named TR6. The predicted protein is 411 amino acids long with a hydrophobic membrane spanning region indicating that at least one form of TR6 is expressed as a membrane bound protein. Comparison of TR6 protein sequence, with other TNF receptor family proteins indicates that it has two of the cysteine-rich repeats characteristic of the extracellular domains of this family, and an intracellular death domain. Northern blot of TR6.

Various tissues and cell lines were screened for mRNA expression by Northern blot. RNA was prepared from cells and cell lines using Tri-Reagent (Molecular Research Center Inc., Cincinnati, Ohio), run in denaturing agarose gels (Sambrook et al., Molecular Cloning: a laboratory manual, 2nd Ed. Cold Spring Harbor Lab Press, N.Y. (1989)) and transfered to Zeta-probe nylon membrane (Biorad, Hercules, Calif.) via vacuum blotting in 25 mM NaOh for 90 min. After neutralization for 5–10 minutes with 1M tris-HCl, pH 7.5 containing 3M NaCl, the blots were prehybridized with 50% formamide, 8% dextran sulfate, 6×SSPE, 0.1%SDS and 100 mg/ml of sheared and dentured salmon sperm DNA for at least 30 min. At 42° C. cDNA probes were labeled with 32P-CTP by random priming (Statagene, La Jolla, Calif.), briefly denatured with 0.25M NaOH and added to the prehybridization solution. After a further incubation for at least 24 h at 42° C., the blots were washed in high stringency conditions and exposed to X-ray film.

Very high expression of TR6 RNA was detected in aortic endothelial cells. High expression was also detected in monocytes. Low expression was detected in bone marrow and CD4+ activated PBLs. Very low, but detectable levels of TR6 RNA was expressed in CD19+ PBLs, CD8+ PBLs (both activated and unstimulated), and unstimulated CD4+ PBLs.

In hematopoietic cell lines, low levels of TR6 RNA was expressed in HL60 (promyelocyte), KG1a (promyeloblast) and KG1 (myeloblast) cell lines. Very low but detectable levels of TR6 RNA was expressed in U937 (monoblast) and THP-1 monocyte) cell lines.

The major RNA form is 3.8 kb in size.

Expression and TR6-Ig Fusion Protein Purification

TR6 was expressed as Fc chimera by fusing the N terminal amino acids 1–184 (which includes leader sequence) to a Factor Xa protease cleavage site and the hinge Fc region of a human IgG-γl heavy cvhain in COS-FcLink (S. Kumar et al., J. Biol. Chem. 270:27905–27913 (1995); K. Johanson et al. J. Biol. Chem. 270:9459–9471 (1995)). This protein was expressed by transfection into CHO cells.

29.5L of conditioned media from CHO cells expressing TR6-Ig (also described herein as TR6-Fc) was applied to a 2.6x11 cm (216 ml) Protein A Sepahrose, fast flow column (Pharmacia) equilibrated in 20 mM sodium phosphate, 150 mM sodium chloride, pH 7 (PBS). The column was washed with PBS and eluted with 100mM glycine, pH 2.5. The eluate (pH 3.3) was immediately adjusted to pH 7 with 2M Tris, pH 8 and dialyzed vs. PBS. 1.3 g of TR6-Ig was recovered at 95% purity by SDS-PAGE gel.

N-terminal sequence of the final mature processed protein, after the cleavage of the leader sequence was experimentally determined to be ALITQQDLAP ( SEQ ID NO: 8). The MW was determined to be 110,528 Da by MALDI Mass Spec. Consistent with this, TR6-Ig ran as the expected dimer in non-denaturing conditions on SDS-PAGE and size exclusion chromatography. The endotoxin level was 5.6eU/mg (gel clot assay). Thus the biology of TR6-Ig refers to the biology of SEQ ID NO:7 polypeptide without the leader sequence.

In vitro Biological Activity of TR6-Ig.

The effect of TR6-Ig on induction cytokine and eicosanoid production by monocytes was evaluated. Freshly isolated and purified monocytes were stimulated with LPS and evaluated for the production TNF-α:, IL-1, IL-6 and IL-8 and PGE2. TR6-Ig inhibits TNF-α and $PGE_2$ production from LPS stimulated monocytes, slightly enhances IL-6 production in some donors, and has little effect on IL-1β and IL-8 production.

In vivo Biological Activity of TR6-Ig.

Single Dose Pharmacokinetics of TR6-Fc in Rats (iv and sc)

With a view to evaluating the in vivo biological activities of TR6, the pharmacokinetics of TR6-Ig were studied in male Sprague-Dawley Rats following iv (1 mg/kg) or sc (3 mg/kg) administration. Rat plasma was assayed for TR6-Ig using a time-resolved fluorescence immunoassay method. In the assay, plasma TR6-Ig was captured on a microtiter plate with goat anti-human polyclonal antibody (IgG Fc specific) and the complex was detected with rabbit anti-TR6 polyclonal antibody. The lower limit of quantification of the assay was 1.0 ng/mL.

Following iv administration, TR6-Ig plasma concentrations declined in a bi-phasic manner. The majority of the area under the plasma concentration versus time curve (88%) was associated with the secondary phase. This kinetically dominant phase was characterized by a half-life of 84 hrs.

Following sc administration (3 mg/kg), maximal plasma concentrations of approximately 19 ug/mL were observed 48 hours after dosing . Thereafter, TR6-Ig declined monoexponentially to one week when concentrations exceeded 9.6 ug/mL. Comparison of the exposure following iv and sc administration suggested TR6-Fc was well absorbed from the subcutaneous injection site into the systemic circulation.

TR6-Ig was evaluated in the mouse air-pouch granuloma model of inflammation and angiogenesis as described using the method based on Colville-Nash et al (J. Pharmacol. Exp. Therap., Vol: 274: 1463–1472) and also recently described in J. Jackson et al (J. Pharmacol. Exp. Therap., Vol: 284: 687–692). Briefly, granulomatous tissue was induced through the introduction of 3 ml of air into the dorsal subcutaneous tissue in anesthesized animals (day 0) followed one day later (day 1) by the injection of 0.5 ml of 0.1% croton oil in complete freundt's adjuvant. Animal were dosed with TR6-Ig on days 1 and 3 at the indicated doses. Cytokine and eicosanoid level in the granuloma were measured on day 6 as previously described. The granuloma tissue dry and wet weights were also evaluated. Angiogenesis was measured by two methods and represented as vascular index: a) by FITC-dextran or carmine dye uptake or b) by immunohistochemical method using CD31 (PECAM-1) as a marker of vessel wall endothelial cells.

In this model, TR6-Ig strongly inhibited LTB4 and LTC4 and $PGE_2$ and TNF-α but not IL-1β production. It also strongly inhibited angiogenesis, primarily the formation of microvasculature, but had no effect on the tissue dry and wet weights.

The ability of TR6-Ig to inhibit the production of inflammatory mediators and cytokines both in vitro and in vivo, combined with its anti-angiogenic properties in vivo, suggest that it may find utility as a protein therapeutic for chronic inflammatory, autoimmune or allergic conditions such as rheumatoid arthritis, psoriasis and asthma. In addition, its anti-angiogenic properties indicate that it may have utility in the treatment of various ailments, such as cancer or arthritis, by starving the tumor or diseased tissue of the oxygen and nutrients it would otherwise receive through newly formed blood vessels.

What is claimed is:

1. An isolated polypeptide comprising the amino acid sequence of SEQ ID NO: 2.

2. The isolated polypeptide of claim 1 that consists of the amino acid sequence set forth in SEQ ID NO:2.

* * * * *